United States Patent
Boyd et al.

(10) Patent No.: US 9,242,125 B2
(45) Date of Patent: Jan. 26, 2016

(54) ORAL COMPOSITION CONTAINING NON-AGGREGATED ZINC NANOPARTICLES

(75) Inventors: Thomas J. Boyd, Metuchen, NJ (US); Guofeng Xu, Princeton, NJ (US); David Viscio, Monmouth Junction, NJ (US); Abdul Gaffar, Princeton, NJ (US); Evangelia S. Arvanitidou, Princeton, NJ (US); Linh Fruge, Hillsborough, NJ (US)

(73) Assignee: COGLATE-PALMOLIVE COMPANY, New York, NY (US)

( * ) Notice: Subject to any disclaimer, the term of this patent is extended or adjusted under 35 U.S.C. 154(b) by 2429 days.

(21) Appl. No.: 11/186,510

(22) Filed: Jul. 21, 2005

(65) Prior Publication Data

US 2007/0020201 A1    Jan. 25, 2007

(51) Int. Cl.
| A61K 8/21 | (2006.01) |
| A61K 33/32 | (2006.01) |
| A61Q 11/00 | (2006.01) |
| A61K 8/27 | (2006.01) |
| B82Y 5/00 | (2011.01) |

(52) U.S. Cl.
CPC . A61Q 11/00 (2013.01); A61K 8/27 (2013.01); B82Y 5/00 (2013.01); *A61K 2800/413* (2013.01)

(58) Field of Classification Search
USPC .................................................... 424/52, 641
See application file for complete search history.

(56) References Cited

U.S. PATENT DOCUMENTS

| 3,946,108 A * | 3/1976 | Tomlinson et al. ............. 424/49 |
| 4,138,477 A | 2/1979 | Gaffar |
| 4,568,540 A | 2/1986 | Asano et al. |
| 4,863,722 A | 9/1989 | Rosenthal |
| 5,000,944 A | 3/1991 | Prencipe et al. |
| 5,330,748 A | 7/1994 | Winston et al. |
| 5,374,418 A * | 12/1994 | Oshino et al. .................... 424/49 |
| 5,385,727 A | 1/1995 | Winston et al. |
| 5,455,023 A | 10/1995 | Giacin et al. |
| 5,455,024 A | 10/1995 | Winston et al. |
| 5,500,448 A | 3/1996 | Cummins et al. |
| 5,503,840 A * | 4/1996 | Jacobson et al. ............. 424/421 |
| 5,578,295 A | 11/1996 | Francis et al. |
| 6,537,360 B2 * | 3/2003 | Miyama et al. ................. 106/35 |
| 6,669,929 B1 | 12/2003 | Boyd et al. |
| 6,723,305 B2 | 4/2004 | DePierro et al. |
| 6,846,478 B1 | 1/2005 | Doyle et al. |
| 7,763,235 B2 | 7/2010 | Boyd et al. |
| 2004/0013616 A1 * | 1/2004 | Witham et al. ................. 424/49 |
| 2004/0136924 A1 | 7/2004 | Boyd et al. |
| 2005/0106112 A1 | 5/2005 | Boyd et al. |
| 2008/0138369 A1 | 6/2008 | Boyd et al. |
| 2008/0160056 A1 | 7/2008 | Boyd et al. |

FOREIGN PATENT DOCUMENTS

| CA | 2320269 | 8/1999 |
| CA | 2332490 | 11/1999 |
| CA | 2431004 | 12/2001 |
| EP | 0 426 213 | 5/1991 |
| EP | 0697861 | 2/1996 |
| EP | 1 072 253 | 1/2001 |
| JP | H02-237910 A | 9/1990 |
| JP | H05-070358 A | 3/1993 |
| JP | 6-65034 | 3/1994 |
| JP | H09-002926 A | 1/1997 |
| JP | H10-236822 A | 9/1998 |
| JP | 11 246375 | 9/1999 |
| JP | 2000-247852 A | 9/2000 |
| JP | 2000-355515 A | 12/2000 |
| JP | 2001-278725 A | 10/2001 |
| JP | 2002-515413 A | 5/2002 |
| WO | WO 01/82922 | 11/2001 |
| WO | WO 2004/054531 | 7/2004 |
| WO | WO 2004/060335 | 7/2004 |
| WO | WO 2008/002922 | 1/2008 |

OTHER PUBLICATIONS

Canadian Patent Office Action dated Dec. 10, 2009 from the Canadian Patent Office for corresponding Canadian Patent Application 2615601.
International Search Report and Written Opinion in International Application No. PCT/US06/028090 mailed Dec. 8, 2006.
Product Catalog of Sumitomo Osaka Cement Co., Ltd., 2003.
Ramanovsky et al., 2004, "Nanocomposites as Functional Materials," Sorosovkiy Education Journal 8(2):50-55 http://window.edu.ru/window_catalog/files/r21287/0402_050.pdf.
Chu et al., "A Study of zinc oxide whiker/nano-ZnO Composite Antimicrobials," Materials Review, Jun. 2003, 17(6).

* cited by examiner

*Primary Examiner* — Adam C Milligan

(57) ABSTRACT

An oral composition comprising a vehicle and a zinc ion source in the form of nanoparticles that are substantially non-aggregated and methods for use of such compositions are described. The composition provides antiplaque and anti malodor benefits to the user and the inclusion of nanoparticles permits a reduction in the amount of zinc ions present in the composition while maintaining efficacy.

18 Claims, 1 Drawing Sheet

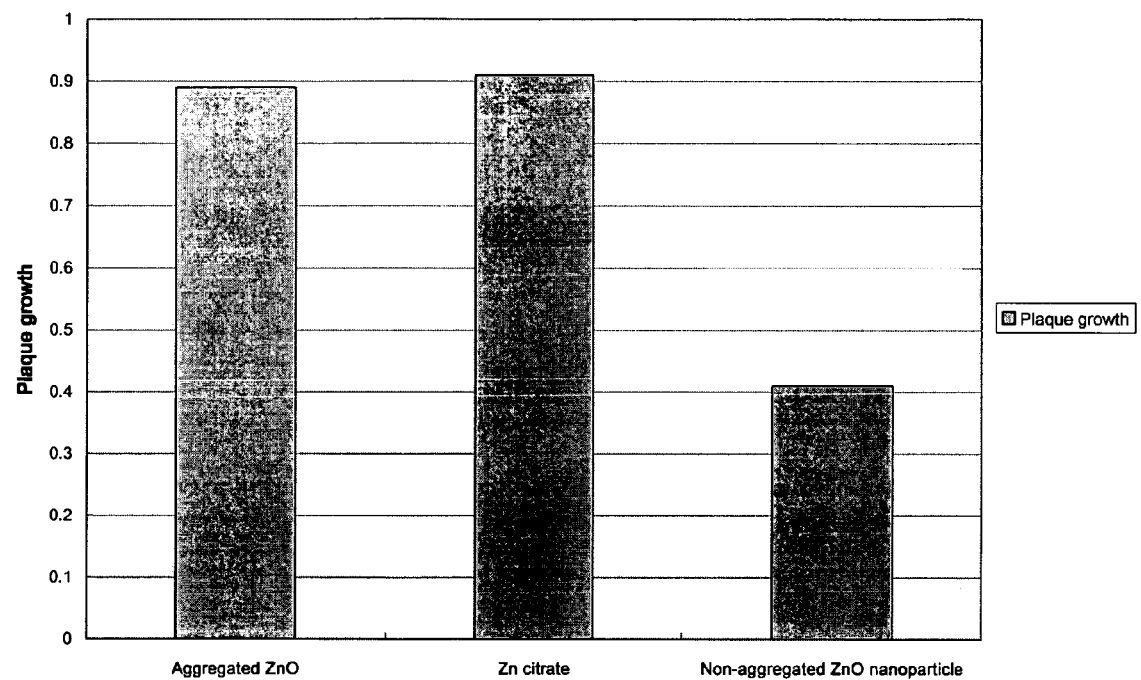

ORAL COMPOSITION CONTAINING NON-AGGREGATED ZINC NANOPARTICLES

BACKGROUND OF THE INVENTION

Zinc ions in an oral care formulation provide users with a number of beneficial effects. For example, zinc ions are known to have antiplaque, anticalculus, and deodorant properties. However, zinc is associated with numerous negative organoleptic properties: for example, astringency and unpleasant lingering tastes. These properties restrict the use of zinc ion-providing compounds in oral care products as a practical matter for products having negative organoleptic properties are not acceptable to consumers. Furthermore, some zinc salts such as zinc oxide have low water solubility and the activity of those zinc salts in the operating environment is typically lower than other zinc forms. This is another limitation in using zinc source in an oral care product.

A dentifrice comprising aggregated zinc oxide particles and a liquid vehicle in an amount sufficient to provide the desired consistency is known in the art. However, an oral compound containing substantially non-aggregated zinc nanoparticles, which enables use of small amounts of zinc ion without influencing activity of the zinc ion under operating environment, has not been reported yet. It is desirable to provide an oral composition which contains low level of zinc ion source but has the same or better beneficial effect of zinc ion in addition to solving the taste problem.

BRIEF SUMMARY OF THE INVENTION

There is provided an oral composition including a vehicle and a zinc ion source in the form of nanoparticles which are substantially non-aggregated. The non-aggregated zinc nanoparticles may be present in an amount of less than about 1% by weight and size of nanoparticles may be about 1 to about 250 nm.

The oral composition having zinc nanoparticles further comprises one or more therapeutic agents such as anticaries agent and antibacterial agent, for example, triclosan, fluoride ions, or stannous ions.

In another embodiment, there is provided a film including a zinc ion source in the form of nanoparticles which are substantially non-aggregated. The non-aggregated zinc nanoparticles may be present in an amount of less than about 1% by weight and size of nanoparticles may be about 1 to about 250 nm.

There is further provided a method of maintaining or promoting the systemic health of human or animal. The method comprises a step of administering to the oral cavity the composition that contains a zinc ion source in the form of nanoparticles which are substantially non-aggregated.

BRIEF DESCRIPTION OF THE DRAWINGS

FIG. 1 is a bar graph chart showing effects of aggregated ZnO, Zn citrate, and non-aggregated ZnO particle against in vitro plaque growth.

DETAILED DESCRIPTION OF THE INVENTION

The present invention relates to an oral composition that may be used to prevent or reduce the formation of plaque; the development of gingivitis, periodontitis, and/or oral tissue inflammation; bad breath; and/or the initiation of systemic inflammatory cascade. More particularly, the invention relates to an oral dentifrice composition including a zinc ion source in the form of nanoparticles which are substantially non-aggregated.

The present invention arises from the finding that non-aggregated, nanoparticle sized zinc ion sources in an oral composition not only provides several oral and/or systemic benefits, but also permits the formulator to reduce the amount of zinc ion source used in the formulation, while retaining a desirable efficacy level. This reduction serves to ameliorate the negative organoleptic properties associated with conventional zinc ion-containing compositions, as well as enhancing formula clarity.

As referred to herein, an "oral composition" is any composition that is suitable for administration or application to a human or animal subject for enhancing the health, hygiene or appearance of the subject, including the prevention or treatment of any physiologic disorder The compositions of the invention include a zinc nanoparticle. Preferably the particle has a size in the nano-range, i.e., about 1 to about 1000 nm. Preferably the nanoparticles have an average particle size (APS) of about 1 µm to about 850 nm, about 50 µm to about 150 nm, about 15 nm to about 500 nm, about 30 nm to about 250 nm and/or about 5 µm to about 100 nm.

The zinc nanoparticles used in the composition of the invention are non-aggregated. By non-aggregated it is meant that the nanoparticles of the invention are not massed into a cluster having a size greater than about 1 micron, preferably greater than about 950 nm or 850 nm. It is found that non-aggregated zinc nanoparticles show antiplaque efficacy under some circumstances that is greater or similar to that of aggregated zinc ion sources. FIG. 1 shows a comparison of the in vitro efficacies of compositions containing (i) non-aggregated zinc oxide nanoparticles, (ii) aggregated zinc oxide and (iii) zinc citrate.

However, zinc nanoparticles may be mixed with aggregated nanoparticles and or zinc ion sources that have an APS of greater than 1 micron, if desired. Preferably, more than 80% of nanoparticles to be incorporated into a formulation are non-aggregated. More preferably, more than 90% of nanoparticles are non-aggregated.

The compositions may contain the non-aggregated zinc nanoparticles in any amount. However, use of a zinc ion source in accordance with the invention can be reduced compared to the amount used in conventional oral formulations providing zinc ion without substantially sacrificing efficacy. Preferably, the oral composition comprises less than about 1% by weight of zinc ion source, with amounts of about 0.3 to about 0.7% by weight and 0.5% to about 0.9% by weight being more preferred.

The zinc ion source for the inventive composition may be any source known or developed in the art or any combination or mixture of such sources. For example, any zinc salt and/or compound may be employed as zinc ion source and such zinc ion source, including water soluble and insoluble, organic and inorganic zinc salts. Examples of suitable zinc compounds that may be employed include, but are not limited to, zinc acetate, zinc acetylacetonate, zinc ammonium sulfate, zinc benzoate, zinc bromide, zinc beryllium orthosilicate, zinc borate, zinc butylphthalate, zinc butylxanthate, zinc caprylate, zinc carbonate, zinc chloroanilate, zinc chlorate, zinc chromate, zinc citrate, zinc cyclohexanebutyrate, zinc chloride, zinc gallate, zinc fluoride, zinc alpha-glucoheptonate, zinc gluconate, zinc glycerophosphate, zinc hydroxide, zinc 8-hydroxyquinoline, zinc 12-hydroxystearate, zinc iodide, zinc acrylate, zinc oxide, zinc propionate, zinc isovalerate, zinc D-lactate, zinc DL-lactate zinc laurate, zinc hexafluorosilicate, zinc methacrylate, zinc molybdate, zinc naphthenate, zinc octoate, zinc oleate, zinc orthophosphate, zinc phenolsulfonate, zinc pyridine-2-thiol-1-oxide, zinc pyrophosphate, zinc resinate, zinc salicylate, zinc sulfate, zinc nitrate, zinc selenide, zinc stearate, zinc sulfanilate, zinc tartrate, zinc tellurate, zinc tungstate, zinc valerate, zinc vanadate, zinc tribromosalicylanilide, and zinc ricinoleate. Preferably, zinc oxide may be used as zinc ion source of the oral composition.

The non-aggregated zinc nanoparticles may be provided in a composition of any form. It may be incorporated neat into e.g., a gel, fluid, solid or paste compositions, or, it may be, for example, provided in the form of zinc ion nanoparticles adsorbed to a particle, incorporated into an emulsion, a particle, a micelle, a core-shell polymer delivery device and/or film composition. These delivery form a may be themselves incorporated into, e.g., a gel, fluid, solid or paste compositions or may be provided to the oral cavity as-is.

In one embodiment, the non-aggregated zinc nanoparticles are present in a film. The structure of the film may be any desired as long as it does not significantly hinder the efficacy of the zinc nanoparticles. The film can be, for example, either mono-layered or multi-layered. The film can be made one of film formats known in the art such as, for example, polymer, woven or non-woven textiles, or pressed or laminate materials. The film may be formed from a matrix comprised of hydroxyalkyl methylcellulose, starch and starch film forming agents or a therapeutic agent such as an antibacterial agent. The film matrix may further comprise water, additional film forming agents, plasticizing agents, surfactants, a flavorant, sweetener or colorant and emulsifying agents.

In one embodiment, one may prepare a film by dissolving a hydroxyalkylmethyl cellulose, a starch ingredient, a colorant, flavor, sweetener and/or therapeutic agents and other film forming ingredients compatible solvent to form a film forming composition. The film forming composition is cast on a releasable carrier and dried to form a sheet of film. Drying of the film may be carried out at high temperature using a drying oven, drying terminal, vacuum drier, or any other suitable drying equipment which does not adversely affect the ingredients of which the film is composed.

Films may have any compositions however, a suitable film forming agent used to prepare the film of the present invention may be a hydroxyalkyl cellulose such as hydroxypropyl cellulose, hydroxyethylpropyl cellulose, hydroxybutyl methyl cellulose, hydroxy propyl methyl cellulose and carboxymethyl cellulose. Preferably the cellulose polymer is a low viscosity hydropropylmethyl cellulose polymer (HPMC). When HPMC is used as the film forming agent, it is preferred that the HPMC have a viscosity in the range of about 1 to about 200 millipascal seconds (mPa·s) as determined as a 2% by weight aqueous solution of the HPMC at 20° C. using a Ubbelohde tube viscometer. Preferably the HPMC has a viscosity of about 3 to about 75 mPa·s at 20° C.

The film containing non-aggregated zinc nanoparticles may be processed to various known types of commercial products such as, for example, tooth tapes, film flakes, strips, and patches. Further, the film itself may be incorporated into other oral care products such as mouthwash, toothpaste, liquid whitener, chewing gum, bead, chew, and lozenge. The film in an oral care product may also be used for decorative purpose as well as for oral care objectives. The film may be formed into decorative shapes such as hearts, stars, diamonds, squares and circles.

In one embodiment, the oral composition having non-aggregated zinc nanoparticles can be used in a method of maintaining or promoting the system health of human or animal by administering the composition to the oral cavity. Typically, the method contains a step of administering an effective amount of the oral composition to the oral cavity of human or animal subject, thereby maintaining oral care or oral hygiene, or improving oral appearance. The oral composition to be used in the method can be further processed to different types of final products so as to meet consumer needs. For example, the composition to be administered to human or animal may be in a form selected from mouthwash, toothpaste, liquid whitener, chewing gum, bead, chew, and lozenge.

In accordance with one embodiment, an oral composition having zinc nanoparticles may further contain one or more therapeutic agents to improve or strengthen oral hygiene efficacy of the composition. Substances conventionally known or used as therapeutic agents in an oral care product may be employed for the oral compositions of the invention. Typically, the therapeutic agent is selected from an anticaries agent or antibacterial agent. Examples of the therapeutic agent may include triclosan, stannous ion, anti-inflammatory agents, anti-oxidant agents, anti-sensitivity agents, whitening agents, fluoride ions, honokiol, magnolol, an arginate ester, cetyl pyrinidium salts, and arginine salts, such as ethyl lauroyl arginine hydrochloride (ELAH).

The therapeutic agent is present in an amount of about 0.1% to about 5% by weight, preferably about 0.2% to about 1% by weight.

In the preparation of the oral composition in accordance with the present invention there is utilized an orally acceptable vehicle. Any known or to be developed in the art may be included. The vehicle may include a water phase with humectant which is preferably glycerine or sorbitol or an alkylene glycol such as polyethylene glycol or propylene glycol, wherein the water is present in amount of about 5% to about 80% by weight and the glycerine, sorbitol and/or the alkylene glycol ingredients total about 5% to about 80% by weight of the dentifrice, more typically about 30% to about 45% by weight.

The oral composition may further contain an inorganic or a natural or synthetic thickener or gelling agent in proportions of about 1% to about 10% by weight, preferably about 1% to about 3% by weight. Suitable thickeners or gelling agents useful in the practice of the present invention include inorganic thickening silicas such as Irish moss, iota-carrageenan, gum tragacanth, polyvinylpyrrolidone, and amorphous silicas available from Huber Corporation, Edison, N.J., United States of America under the trade designation ZEODENT® 165.

Polishing agents such as silica, calcined alumina, sodium bicarbonate, calcium carbonate, dicalcium phosphate and calcium pyrophosphate may be included in the oral compositions used in the practice of the present invention. Visually-clear dentifrice compositions are obtained by using polishing agents such as colloidal silica, such as those sold under the trade designation ZEODENT® 115 available from the Huber Corporation, Edison, N.J., United States of America, or alkali metal aluminosilicate complexes (that is, silica containing alumina combined in its matrix). These polishing agents desirably have refractive indices close to the refractive indices of gelling agent-liquid (including water and/or humectant) systems used in dentifrice compositions. The polishing agent is generally present in the oral composition in weight concentrations of about 10% to about 50% by weight.

Surfactants are used in the oral compositions of the present invention to achieve increased prophylactic action and render the instant compositions more cosmetically acceptable. Suitable examples of surfactants include water-soluble salts of higher fatty acid monoglyceride monosulfates, such as the sodium salt of the monsulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of these are N-lauroyl sarcosine, and the sodium, potassium, and ethanolamine salts of N-lauroyl, N-myristoyl, or N-palmitoyl sarcosine. The anionic surfactants are typically present in the oral compositions of the present invention in an amount of about 1% to about 15% by weight, preferably about 5% to about 10% by weight.

Any other additives known or developed for use in oral care compositions may be incorporated into the composition, including anti-caries agents, flavorants, colorants, other active agents, whitening compounds, anti-tarter compounds, anti-sensitizing compounds, vitamins, herbs and other botanicals, anti-inflammatory agents, anti-oxidant compounds, hormones, and other proteins or peptides.

To prepare the oral composition of the present invention, water, humectants, e.g. glycerin, sorbitol polyethylene glycol are dispersed in a conventional mixer until the mixture becomes a homogeneous gel phase. Into the gel phase are added the polishing agent. These ingredients are mixed until a homogeneous phase is obtained. Thereafter, the thickener, any flavor and surfactant ingredients are added and the ingredients mixed at high speed until vacuum of about 20 to 100 mmHg.

The invention is further illustrated but not limited by the following examples. Variations of the following examples are possible without departing from the scope of the invention.

EXAMPLES

Examples 1-5

Oral compositions containing various levels of zinc oxide nanoparticles were prepared by using the ingredients listed in Table I below. Each composition has the same ingredients of the same amount except that levels of zinc oxide nanoparticles are range from 0% through 2.0%.

TABLE I

| Ingredient | Example 1 | Example 2 | Example 3 | Example 4 | Example 5 |
|---|---|---|---|---|---|
| Sodium CMC | 0.65% | 0.65% | 0.65% | 0.65% | 0.65% |
| Polyethylene glycol 600 (PEG-12) | 3.0% | 3.0% | 3.0% | 3.0% | 3.0% |
| Sorbitol | 57.69% | 57.69% | 57.69% | 57.69% | 57.69% |
| Sodium saccharin | 0.3% | 0.3% | 0.3% | 0.3% | 0.3% |
| Sodium fluoride | 0.24% | 0.24% | 0.24% | 0.24% | 0.24% |
| Tetrasodium pyrophosphate | 0.5% | 0.5% | 0.5% | 0.5% | 0.5% |
| FD&C Blue #1 dye (1% in water) | 0.004% | 0.004% | 0.004% | 0.004% | 0.004% |
| Silica abrasive (ZEODENT ® 115) | 20% | 20% | 20% | 20% | 20% |
| Silica thickener (ZEODENT ® 165) | 4.25% | 4.25% | 4.25% | 4.25% | 4.25% |
| Flavor oil | 1.15% | 1.15% | 1.15% | 1.15% | 1.15% |
| Sodium lauryl sulfate | 1.5% | 1.5% | 1.5% | 1.5% | 1.5% |
| Cocamidopropyl betaine | 0.45% | 0.45% | 0.45% | 0.45% | 0.45% |
| ZnO, nano-particle | 0% | 0.1% | 0.5% | 1% | 2% |
| Propylene glycol | 0% | 0.1% | 0.5% | 1.875% | 3.714% |
| White, flavored films (optional) | 0.3% | 0.3% | 0.3% | 0.3% | 0.3% |
| Water | Q.S. % | Q.S. % | Q.S. % | Q.S. % | Q.S. % |
| Total | 100% | 100% | 100% | 100% | 100% |

In each Example, the ingredients were mixed until a homogenous mixture was formed. The oral compositions of Examples 1-5 were tested to evaluate antiplaque the activity of each. The in vitro tests of the oral compositions for antiplaque activity are shown in Table II below.

TABLE II

| Composition | Plaque growth, in vitro | % Inhibition of Plaque |
|---|---|---|
| Example 1 (placebo) | 0.436 | — |
| Example 2 (0.1% ZnO) | 0.457 | 0% |
| Example 3 (0.5% ZnO) | 0.269 | 38% |
| Example 4 (1.0% ZnO) | 0.268 | 39% |
| Example 5 (2.0% ZnO) | 0.346 | 21% |

Example 6

A slurry formulation to be cast into films was prepared by using common film-forming ingredients, as shown in Table III.

TABLE III

| Ingredient | Example 6 |
|---|---|
| Water | Q.S. |
| HPMC E5 | 10 |
| HPMC E50 | 3 |
| Zinc oxide in water (50% solids) | 17 |
| Canola Oil | 3 |
| Propylene glycol | 6 |
| D&C Red #30 | 0.5 |
| Titanium dioxide | 0.5 |
| Tween 80 | 0.5 |

After casting and drying, the resultant film is cut into approximately square flakes having the dimensions of 1 mm by 1 mm, and is incorporated into a standard gel formulation toothpaste.

Although the invention has been described with reference to specific examples, it will be apparent to one skilled in the art that various modifications may be made thereto which fall within its scope.

We claim:

1. An oral composition comprising a vehicle and zinc oxide in the form of nanoparticles that are more than 90% non-aggregated, the nanoparticles having an average particle size of from about 1 nm to about 850 nm, wherein the zinc oxide is present in an antibacterial amount of from about 0.3 to 1% by weight of oral composition.

2. The oral composition of claim 1, wherein size of the nanoparticles is about 1 to about 250 nm.

3. The oral composition of claim 1, wherein the oral composition further comprises one or more therapeutic agents.

4. The oral composition of claim 3, wherein the therapeutic agent is selected from an anticaries agent and antibacterial agent.

5. The oral composition of claim 4, wherein the therapeutic agent is selected from the group consisting of triclosan, stannous ion, fluoride, arginine salts, and cetyl pyrinidium salts, honokiol and magnolol.

6. The oral composition of claim 1, wherein the oral composition further comprises an ingredient selected from the group consisting of an abrasive, a surfactant, a flavor agent, and a sweetener.

7. A film for incorporation into an oral care composition comprising a zinc ion source in the form of nanoparticles which are more than 90% non-aggregated, the nanoparticles having an average particle size of from about 1 nm to about 850 nm, wherein the zinc ion source is present in an amount of 17% to about 25% by weight, based on the weight of the film, wherein the film comprises a hydroxyalkyl cellulose component selected from hydroxypropyl cellulose, hydroxyethylpropyl cellulose, hydroxybutyl methyl cellulose, hydroxypropylmethyl cellulose, and combinations thereof.

8. The film of claim 7, wherein size of the nanoparticles is about 1 to about 250 nm.

9. The film of claim 7, wherein the zinc ion source is zinc oxide.

10. The film of claim 7, wherein the film further comprises one or more therapeutic agents.

11. A dentifrice comprising the film of claim 7.

12. An oral care article comprising the oral care composition of claim 1, the article comprising an orally acceptable vehicle and from about 0.3 to 1% by weight of zinc oxide nanoparticles that are more than 90% non-aggregated, the nanoparticles having an average particle size of from about 1 to about 850 nm, wherein the oral care article is selected from the group consisting of mouthwash, oral strip, toothpaste, liquid whitener, chewing gum, bead, chew, lozenge and spray.

13. The oral care article of claim 12, wherein the size of the nanoparticles is about 1 to about 250 nm.

14. A method of maintaining or promoting health of human or animal comprising: administering to the oral cavity an effective amount of the composition of claim 1.

15. The method of claim 14, wherein the composition is in a form selected from the group consisting of mouthwash, oral strip, toothpaste, liquid whitener, chewing gum, bead, chew, lozenge and spray.

16. An oral composition comprising a vehicle a zinc ion source in the form of nanoparticles which are more than 90% non-aggregated, and triclosan.

17. The oral composition of claim 1, wherein the vehicle comprises an alkylene glycol.

18. The composition of claim 17, wherein the alkylene glycol is polyethylene glycol.

* * * * *